(12) United States Patent
Kordic et al.

(10) Patent No.: US 12,391,708 B2
(45) Date of Patent: Aug. 19, 2025

(54) CRYSTALLINE LORLATINIB : FUMARIC ACID AND SOLID STATE FORM THEREOF

(71) Applicant: TAPI CROATIA INDUSTRIES LTD, Prigorje Brdovecko (HR)

(72) Inventors: Lorena Kordic, Rab (HR); Ivica Grebenar, Zagreb (HR); Dijana Škalec Šamec, Jastrebarsko (HR)

(73) Assignee: TAPI CROATIA INDUSTRIES LTD, Prigorje Brdovecko (HR)

( * ) Notice: Subject to any disclaimer, the term of this patent is extended or adjusted under 35 U.S.C. 154(b) by 674 days.

(21) Appl. No.: 17/624,870

(22) PCT Filed: Jul. 10, 2020

(86) PCT No.: PCT/US2020/041524
§ 371 (c)(1),
(2) Date: Jan. 5, 2022

(87) PCT Pub. No.: WO2021/011345
PCT Pub. Date: Jan. 21, 2021

(65) Prior Publication Data
US 2022/0289764 A1    Sep. 15, 2022

Related U.S. Application Data

(60) Provisional application No. 62/875,601, filed on Jul. 18, 2019.

(51) Int. Cl.
*C07D 498/18* (2006.01)
(52) U.S. Cl.
CPC ........ *C07D 498/18* (2013.01); *C07B 2200/13* (2013.01)
(58) Field of Classification Search
CPC .... C07D 498/18; C07B 2200/13; A61P 35/00
See application file for complete search history.

(56) References Cited

U.S. PATENT DOCUMENTS

| | | | |
|---|---|---|---|
| 8,680,111 B2 | 3/2014 | Bailey | |
| 9,637,500 B2 * | 5/2017 | Jensen | .................... A61P 35/00 |
| 10,420,749 B2 | 9/2019 | Pencheva | |
| 11,299,500 B2 | 4/2022 | Bowles | |
| 2019/0365712 A1 | 12/2019 | Pencheva et al. | |
| 2021/0163498 A1 | 6/2021 | Skugor et al. | |
| 2024/0190843 A1 | 6/2024 | Brown et al. | |

FOREIGN PATENT DOCUMENTS

| | | | |
|---|---|---|---|
| CN | 110483551 A | 11/2019 | |
| IN | 201941052957 | 6/2021 | |
| IN | 202041000698 | 7/2021 | |
| IN | 202041007370 | 8/2021 | |
| WO | 2013132376 A1 | 9/2013 | |
| WO | 2014207606 A1 | 12/2014 | |
| WO | 2017021823 A1 | 2/2017 | |
| WO | 2017175091 A1 | 10/2017 | |
| WO | 2019073347 A1 | 4/2019 | |
| WO | WO-2019209633 A1 * | 10/2019 | ............. A61P 35/00 |
| WO | 2021069571 A1 | 4/2021 | |

OTHER PUBLICATIONS

Berge et al. Pharmaceutical Salts (Journal of Pharmaceutical Science, 1977, 66, 1-19. (Year: 1977).*
Rolf Hilfiker, et al. "Relevance of Solid-State Properties for Pharmaceutical Products", Polymorphism in the Pharmaceutical Industry, pp. 1-19 (2006).
Stephen Byrn, et al. "Pharmaceutical Solids: A Strategic Approach to Regulatory Considerations", Pharmaceutical Research, vol. 12, No. 7, pp. 945-954 (1995).
Mino R. Caira, "Crystalline Polymorphism of Organic Compounds", Topics In Current Chemistry, vol. 198, pp. 163-208 (1998).
International Search Report and Written Opinion of the International Searching Authority issued in corresponding application PCT/US2020/041524 mailed Sep. 28, 2020 (19 pages).

\* cited by examiner

*Primary Examiner* — Amanda L. Aguirre
(74) *Attorney, Agent, or Firm* — Carter, DeLuca & Farrell LLP (57) ABSTRACT

The present disclosure relates to crystalline Lorlatinib:Fumaric acid, solid state forms thereof, processes for preparation thereof, pharmaceutical compositions and methods of use thereof.

16 Claims, 5 Drawing Sheets

CRYSTALLINE LORLATINIB : FUMARIC ACID AND SOLID STATE FORM THEREOF

CROSS REFERENCE TO RELATED APPLICATIONS

This application is a National Stage of, and claims priority to and the benefit of, International Patent Application No. PCT/US2020/041524 filed Jul. 10, 2020, which, in turn, claims the benefit of and priority to, U.S. Provisional Patent Application No. 62/875,601 filed Jul. 18, 2019.

FIELD OF THE INVENTION

The present disclosure relates to crystalline Lorlatinib: Fumaric acid, solid state form thereof and pharmaceutical compositions thereof.

BACKGROUND

Lorlatinib, described also as PF-6463922, has the chemical name (10R)-7-amino-12 fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile. Lorlatinib is developed for the treatmen of cancer, mainly treating non-small cell lung cancer. Lorlatinib has the following chemical structure:

The amendment does not add new matter.

Lorlatinib is disclosed in U.S. Pat. Nos. 8,680,111 and 9,133,215. Solid state forms of Lorlatinib are disclosed in U.S. Pat. No. 9,637,500 (referred to therein as forms 1, 2 & 3), in International PCT Publication No. 2017/021823 and in International PCT Publication No. 2019/209633.

Lorlatinib salts are also described in the literature. Lorlatinib hydrochloride salt is described in J. Med. Chem. 2014, 57, 4720-4744 (designated as compound 8K) and Lorlatinib maleate salt, forms I and II, is described in International PCT publication No. 2017/175091.

Polymorphism, the occurrence of different crystal forms, is a property of some molecules and molecular complexes. A single compound, like Lorlatinib, may give rise to a variety of polymorphs having distinct crystal structures and physical properties like melting point, thermal behaviors (e.g., measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}C$-) NMR spectrum. One or more of these techniques may be used to distinguish different polymorphic forms of a compound.

Different salts or co-crystals and solid state forms (including solvated forms) of an active pharmaceutical ingredient may possess different properties. Such variations in the properties of different salts or co-crystal and solid state forms may provide a basis for improving formulation, for example, by facilitating better processing or handling characteristics, improving the dissolution profile, or improving stability (polymorph as well as chemical stability) and shelf-life. These variations in the properties of different salts or co-crystals and solid state forms may also provide improvements to the final dosage form, for instance, if they serve to improve bioavailability. Different salts or co-crystals and solid state forms of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts or co-crystals and solid state forms of a pharmaceutical product can provide materials having desirable processing properties, such as ease of handling, ease of processing, storage stability, and ease of purification, or as desirable intermediate crystal forms that facilitate conversion to other salts and co-crystal or polymorphic forms. New polymorphic forms, new salts and co-crystals of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability, which may offer better processing or handling characteristics, improved dissolution profile, or improved shelf-life.

For at least these reasons, there is a need for additional solid state forms of Lorlatinib:Fumaric acid which offers superior properties without altering the pharmacological properties.

SUMMARY OF THE INVENTION

The present disclosure relates to crystalline Lorlatinib: Fumaric acid and a solid state form thereof. The present disclosure also relates to processes for preparation thereof, and pharmaceutical compositions including crystalline Lorlatinib:Fumaric acid or the described solid state form of.

In another embodiment, the present disclosure encompasses use of crystalline Lorlatinib:Fumaric acid or the described solid state form thereof in the preparation of pharmaceutical compositions and/or formulations, optionally for the treatment of cancer, in embodiments treating non-small cell lung cancer.

In another embodiment, the present disclosure encompasses crystalline Lorlatinib:Fumaric acid or the described solid state form thereof for use in the preparation of pharmaceutical compositions and/or formulations, optionally for the treatment of cancer, in embodiments treating non-small cell lung cancer.

The present disclosure further provides pharmaceutical compositions including crystalline Lorlatinib:Fumaric acid or the described solid state form thereof according to the present disclosure.

In yet another embodiment, the present disclosure encompasses pharmaceutical formulations including crystalline Lorlatinib:Fumaric acid or the described solid state form thereof and at least one pharmaceutically acceptable excipient.

The present disclosure encompasses processes to prepare said pharmaceutical formulations of crystalline Lorlatinib: Fumaric acid by combining crystalline Lorlatinib:Fumaric acid or the described solid state form thereof and at least one pharmaceutically acceptable excipient.

Crystalline Lorlatinib:Fumaric acid or the described solid state form thereof can be used as a medicament, in embodiments for the treatment of cancer, as specified above.

The present disclosure also provides methods of treating, in embodiments for the treatment of cancer, as specified above by administering a therapeutically effective amount of crystalline Lorlatinib:Fumaric acid or of the described solid state form thereof, or at least one of the herein described pharmaceutical compositions or formulations, to a subject suffering from cancer or the above specified diseases, or otherwise in need of the treatment.

The present disclosure also provides uses of crystalline Lorlatinib:Fumaric acid of the present disclosure, or of the described solid state form thereof, or at least one of the above pharmaceutical compositions or formulations for the manufacture of medicaments, in embodiments for the treatment of cancer, as specified above.

DETAILED DESCRIPTION OF ILLUSTRATIVE EMBODIMENTS

The present disclosure relates to crystalline Lorlatinib:Fumaric acid and solid state form thereof, processes for preparation thereof, and pharmaceutical compositions comprising the crystalline Lorlatinib:Fumaric acid or of the described solid state form thereof.

The disclosure also relates to conversion of the crystalline Lorlatinib:Fumaric acid or the described form thereof to other forms thereof, Lorlatinib or salts or co-crystals thereof and solid state forms thereof.

Crystalline Lorlatinib:Fumaric acid according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

Crystalline Lorlatinib:Fumaric acid may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Lorlatinib:Fumaric acid referred to herein as being characterized by graphical data "as depicted in" a Figure will thus be understood to include any crystal forms of Lorlatinib:Fumaric acid, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Lorlatinib:Fumaric acid described herein as is substantially free of any other solid state forms would be understood to contain greater than about 80% (w/w), greater than about 90% (w/w), greater than about 95% (w/w), greater than about 98% (w/w), greater than about 99% (w/w), or 100% of the subject solid state form of Lorlatinib:Fumaric acid. Accordingly, in some embodiments of the disclosure, the described solid state form of Lorlatinib:Fumaric acid may contain from about 1% to about 20% (w/w), from about 5% to about 20% (w/w), or from about 5% to about 10% (w/w) of one or more other solid state forms of the Lorlatinib:Fumaric acid.

As used herein, unless stated otherwise, XRPD peaks reported herein are measured using CuKα radiation, λ=1.54184 Å, in embodiments, XRPD peaks reported herein are measured using CuKα radiation, λ=1.54184 Å, at a temperature of 25±3° C.

As used herein, unless stated otherwise, $^{13}$C solid state NMR was measured on 600 MHz at room temperature at a spin rate of 16 kHz.

As used herein, the term "isolated" in reference to crystalline Lorlatinib:Fumaric acid of the present disclosure corresponds to crystalline Lorlatinib:Fumaric acid that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term "anhydrous" is in relation to crystalline Lorlatinib:Fumaric acid of the present disclosure which does not include any crystalline water (or other solvents) in a defined, stoichiometric amount within the crystal. Moreover, an "anhydrous" form does not contain more than about 1% (w/w) or more than about 0.5% of either water or organic solvents as measured, for example, by TGA, Karl Fischer, or by other suitable technique. Preferably, "anhydrous" form as used herein contains 0.25 wt % or less, 0.2 wt % or less, or 0.1 wt % or less of water and organic solvents.

"Co-crystal" as used herein is defined as a crystalline material including two or more molecules which are solids at room temperature in the same crystalline lattice and associated by non-ionic and non-covalent bonds. Co-crystals may comprise a pharmaceutical agent and at least one co-crystal former and may themselves be solvated or unsolvated. In some embodiments, the co-crystal includes two molecules which are in a natural (i.e. non-ionized) state.

The amount of solvent employed in a chemical process, e.g., a reaction or crystallization, may be referred to herein as a number of "volumes" or "vol" or "V." For example, a material may be referred to as being suspended in 10 volumes (or 10 vol or 10 V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding (methyl tert-butyl ether) MTBE (1.5 v/v) to a 100 ml reaction mixture would indicate that 150 mL of MTBE was added.

As used herein, unless otherwise indicated, percentages relate to weight percent (wt %).

Figure 2:
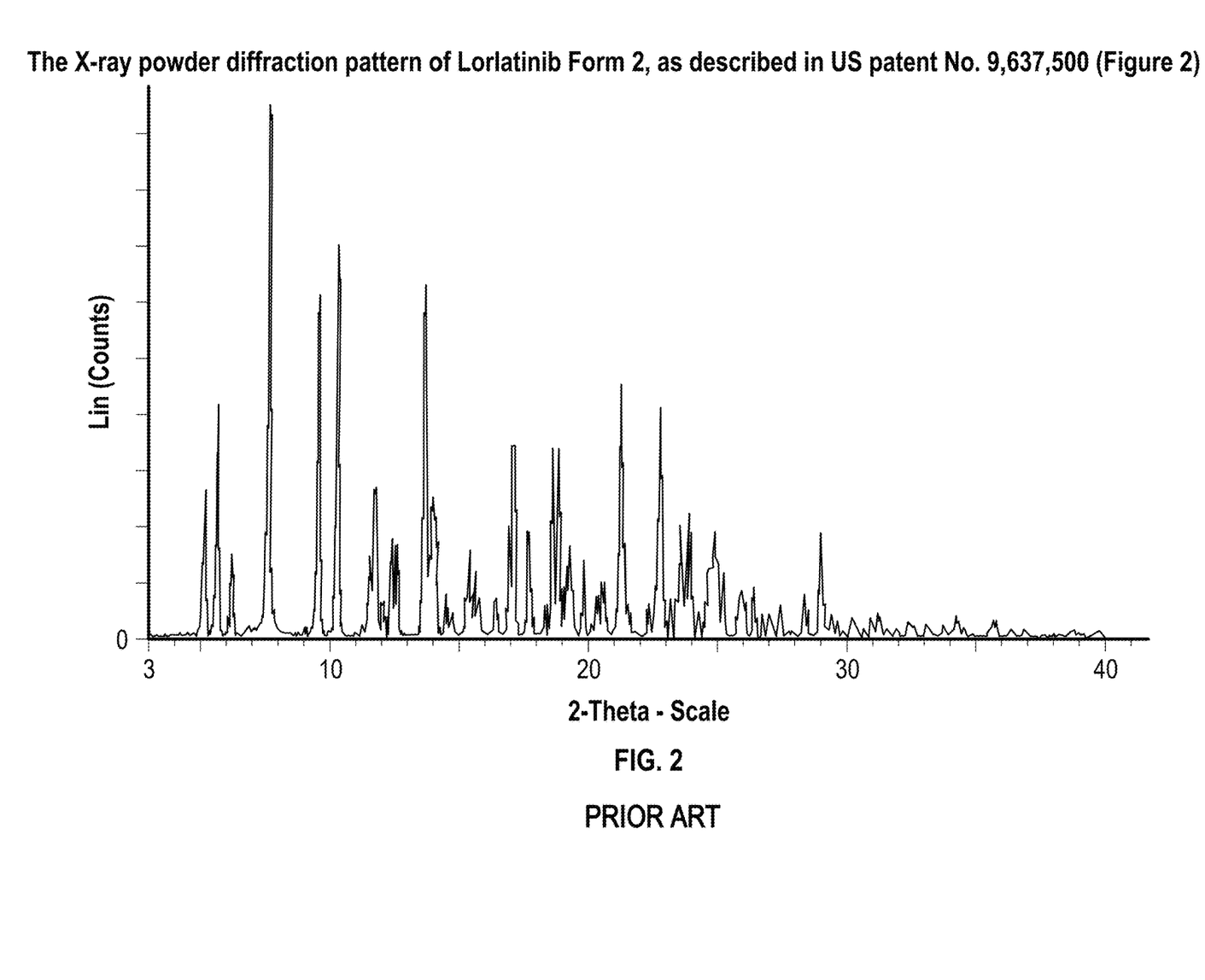
FIG. 2 shows an XRPD pattern of Lorlatinib Form 2, as described in U.S. Pat. No. 9,637,500 (FIG. 2).

As used therein the term "Lorlatinib Form 2" relates to a crystalline form having an XRPD pattern shown herein in FIG. 2, as described in U.S. Pat. No. 9,637,500 (FIG. 2 therein). For example, as defined in U.S. Pat. No. 9,637,500, Lorlatinib Form 2 has an XRPD pattern with characteristic peaks at: 5.6, 7.6, 9.5, 10.2 and 13.6 degrees 2-theta±0.2 degrees 2-theta. Example 2 of U.S. Pat. No. 9,637,500 describes the preparation of Lorlatinib Form 2.

As used herein, crystalline Lorlatinib:Fumaric acid is a distinct molecular species. In one embodiment crystalline Lorlatinib:Fumaric acid may be a co-crystal of Lorlatinib and Fumaric acid.

As used herein, a co-crystal is a crystalline material composed of two or more molecules within the same crystal lattice, wherein the molecules interact with each other via non-ionic interactions.

In embodiments the molar ratio between the active pharmaceutical ingredient (Lorlatinib) and the conformer (Fumaric acid) is between 2:1.5 and 2.5:1, in embodiments between 2:1.25 and 2.25:1, in other embodiments about 2:1.

In embodiments the molar ratio between the active pharmaceutical ingredient (Lorlatinib) and the coformer (Fumaric acid) is between 2:1.5 and 1.5:1, in embodiments between 2:1.25 and 1.25:1, in other embodiments about 2:1.

Figure 1:
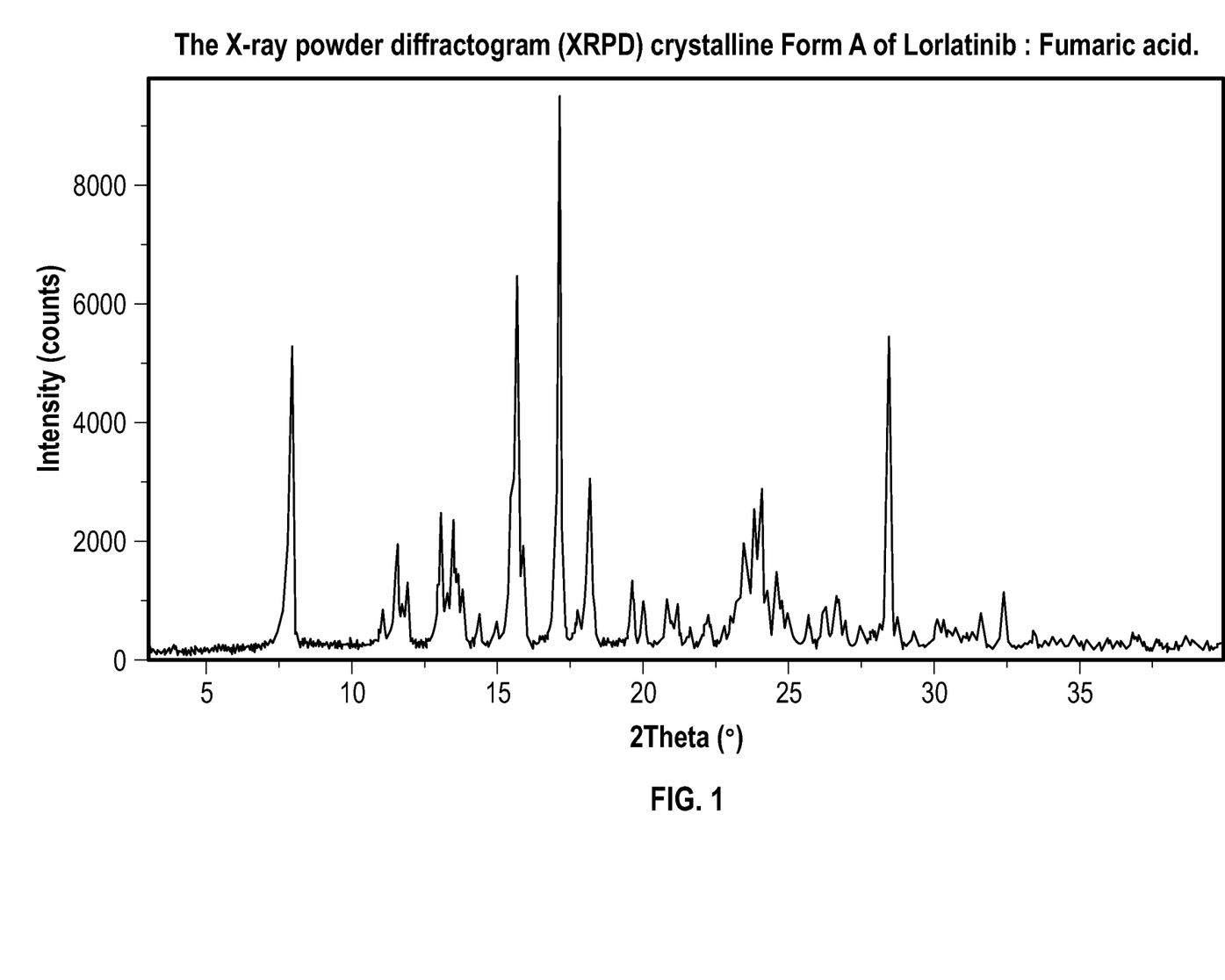
FIG. 1 shows an X-ray powder diffractogram (XRPD) of crystalline Form A of Lorlatinib:Fumaric acid.
Figure 3:
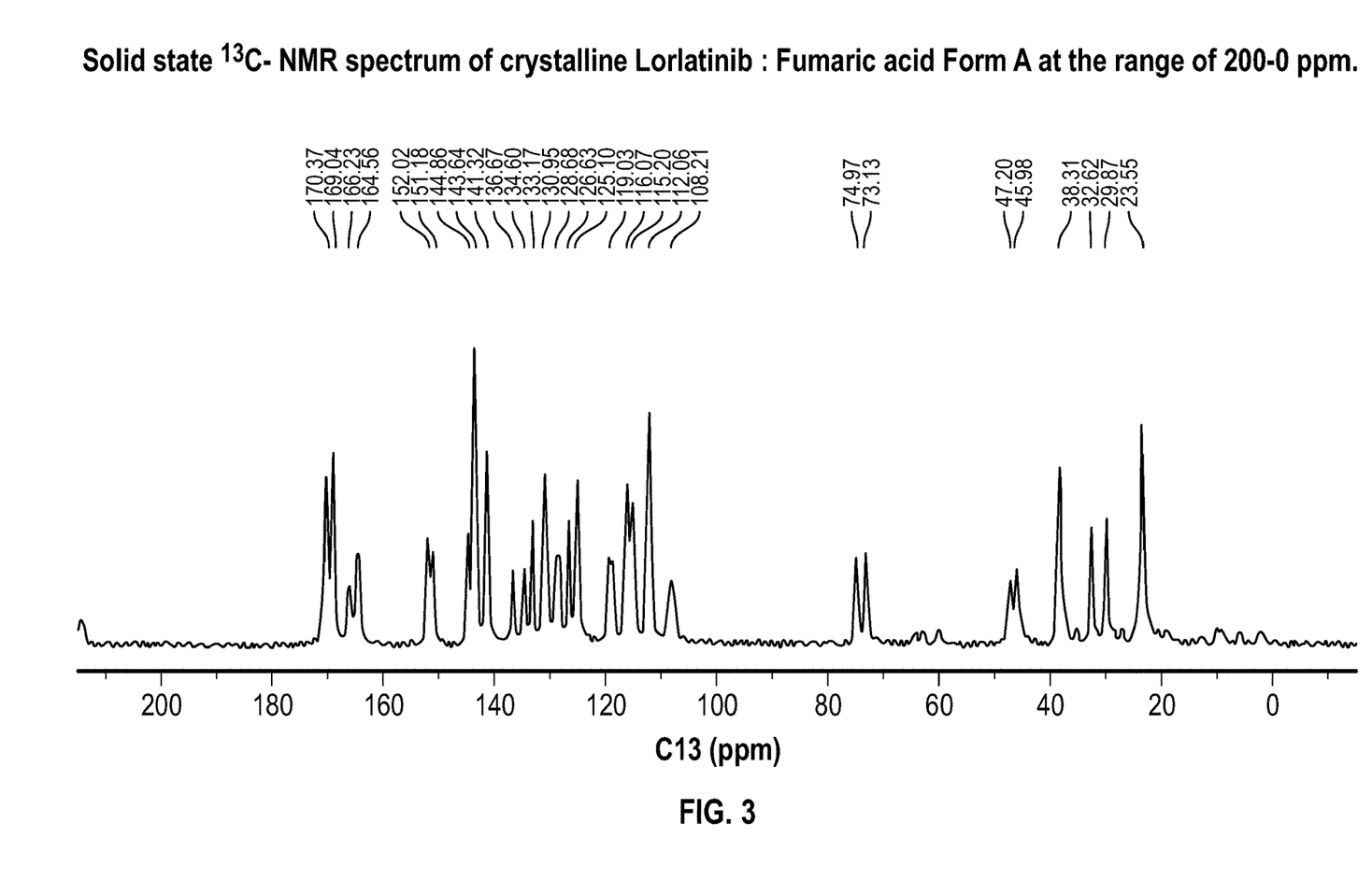
FIG. 3 shows solid state $^{13}$C-NMR spectrum of crystalline Lorlatinib:Fumaric acid Form A at the range of 200-0 ppm.
Figure 4:
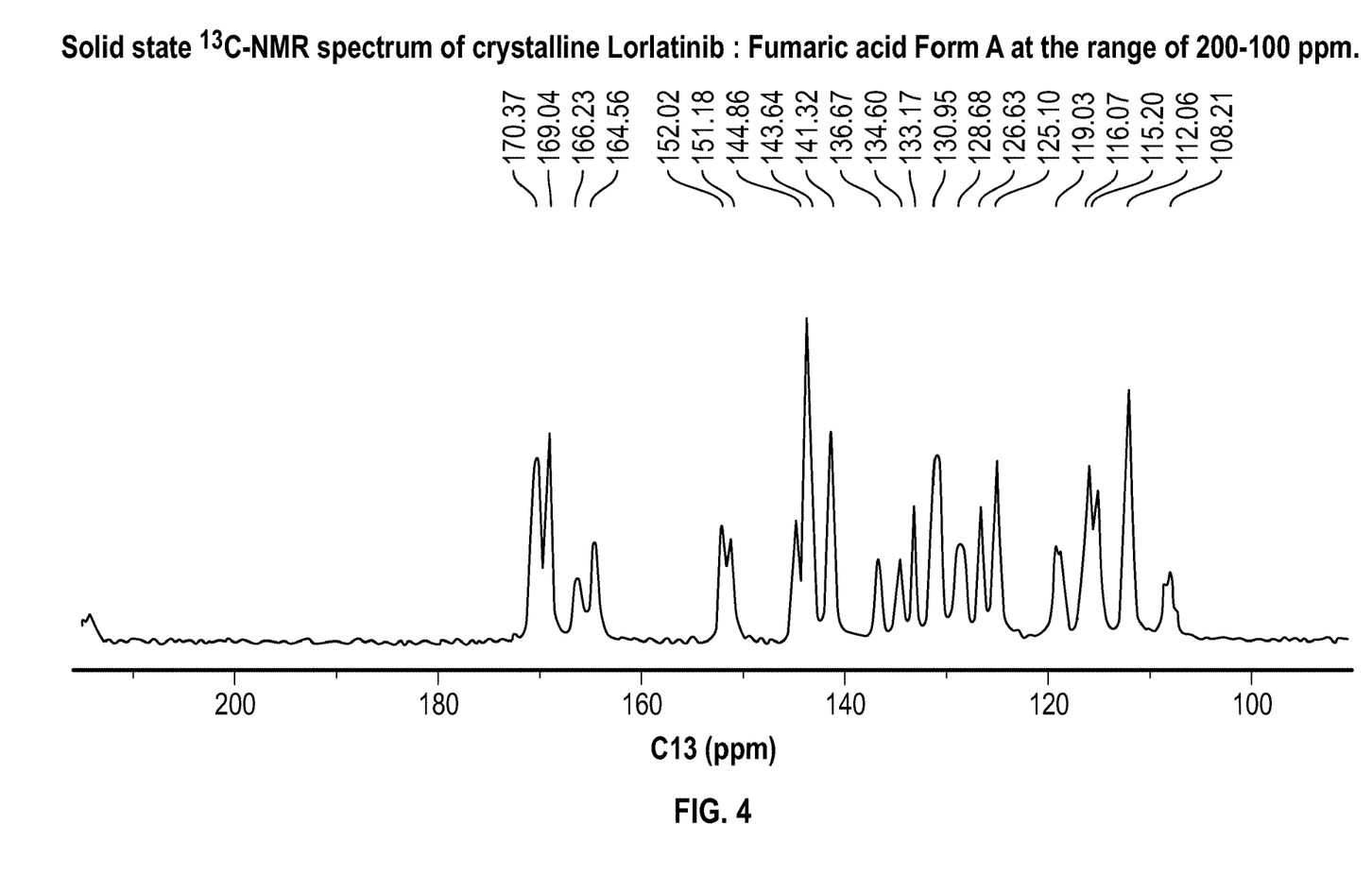
FIG. 4 shows solid state $^{13}$C-NMR spectrum of crystalline Lorlatinib:Fumaric acid Form A at the range of 200-100 ppm.
Figure 5:
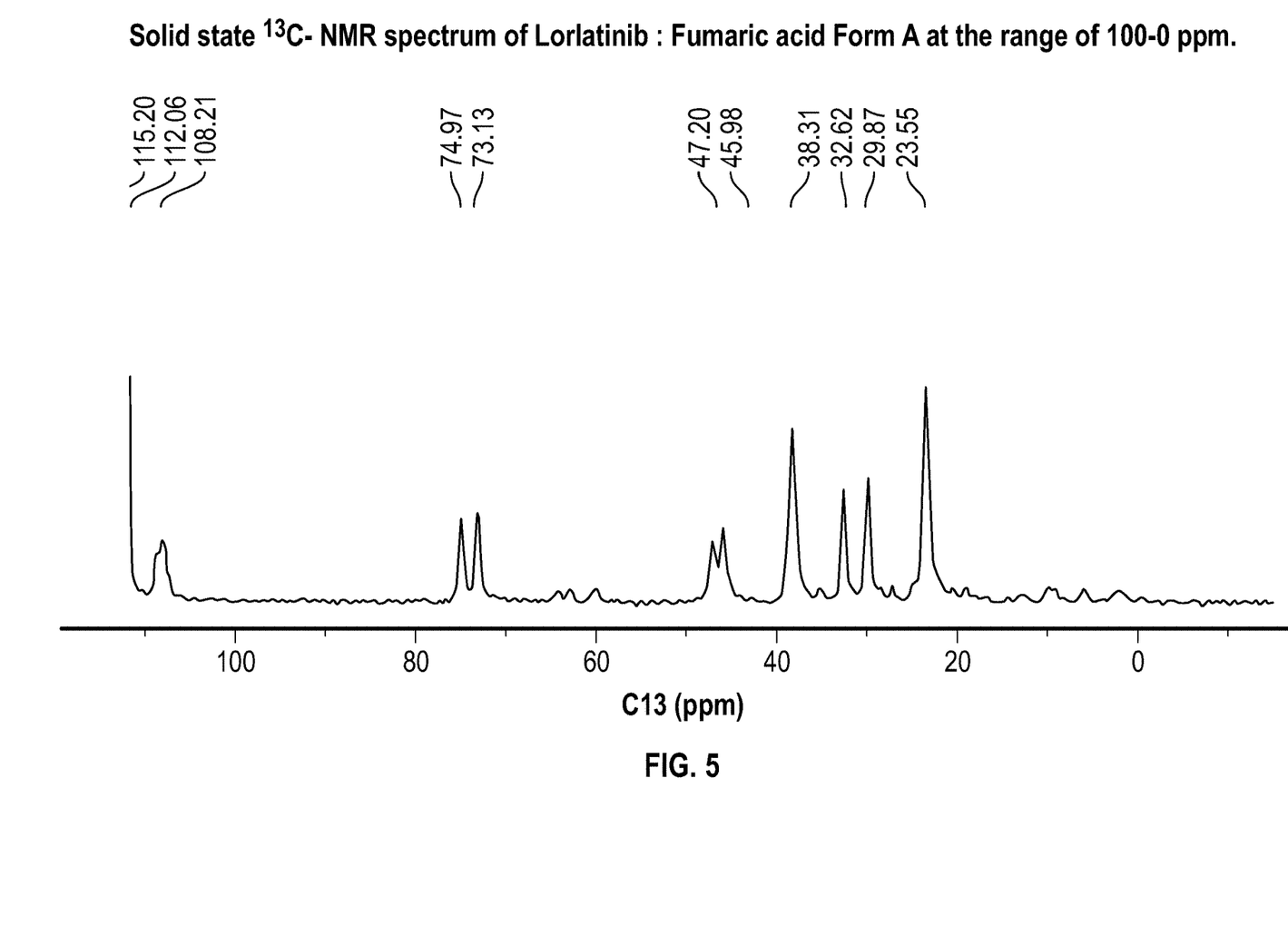
FIG. 5 shows solid state $^{13}$C-NMR spectrum of Lorlatinib:Fumaric acid Form A at the range of 100-0 ppm.

The present disclosure further relates to a crystalline form of Lorlatinib:Fumaric acid designated Form A. The crystalline Form A of Lorlatinib:Fumaric acid may be characterized by data selected from one or more of the following: an XRPD pattern having peaks at 8.0, 11.6, 13.5, 17.1 and 18.2 degrees 2-theta±0.2 degrees 2-theta; an XRPD pattern substantially as depicted in FIG. 1; a solid-state $^{13}$C NMR spectrum with signals at 170.4, 152.0, 141.3, 119.0 and 74.1 ppm±0.2 ppm; a solid state $^{13}$C NMR spectrum having the following chemical shift absolute differences from a peak at 23.6 ppm±2 ppm of 146.8, 128.4, 117.7, 95.4 and 50.5 ppm±0.1 ppm; a solid-state $^{13}$C NMR spectrum as depicted in FIG. 3 or 4 or 5; and combinations of these data.

Crystalline Form A of Lorlatinib:Fumaric acid may be further characterized by an XRPD pattern having peaks at 8.0, 11.6, 13.5, 17.1 and 18.2 degrees 2-theta±0.2 degrees 2-theta, and also having one, two, three, four or five additional peaks selected from 13.1, 14.4, 15.7, 19.6 and 24.1 degrees 2-theta±0.2 degrees two theta.

Alternatively, crystalline Form A of Lorlatinib:Fumaric acid may be characterized by an XRPD pattern having peaks at 8.0, 11.6, 13.1, 13.5, 14.4, 15.7, 17.1, 18.2, 19.6, and 24.1 degrees 2-theta±0.2 degrees 2-theta.

In one embodiment crystalline Form A of Lorlatinib:Fumaric acid may be a co-crystal.

In another embodiment crystalline Form A of Lorlatinib:Fumaric acid may be anhydrous. In embodiments, crystalline Lorlatinib:Fumaric acid Form A contains 0.5% (w/w) or less of water or organic solvents.

In some embodiments crystalline Form A Lorlatinib:Fumaric acid may be isolated.

In another embodiment of the present disclosure, crystalline Lorlatinib:Fumaric acid Form A is polymorphically pure.

In preferred embodiment, crystalline Lorlatinib:Fumaric acid form A contains no more than about 20%, no more than about 10%, no more than about 5%, no more than about 2%, no more than about 1% or about 0% of any other crystalline forms of Lorlatinib:Fumaric acid.

Crystalline Lorlatinib:Fumaric acid Form A may be characterized by each of the above characteristics alone or by all possible combinations, e.g., an XRPD pattern having peaks at 8.0, 11.6, 13.1, 13.5, 14.4, 15.7, 17.1, 18.2, 19.6 and 24.1 degrees 2-theta±0.2 degrees 2-theta; an XRPD pattern as depicted in FIG. 1; a solid-state $^{13}$C NMR spectrum with signals at 170.4, 152.0, 141.3, 119.0 and 74.1 ppm±0.2 ppm; a solid state $^{13}$C NMR spectrum having the following chemical shift absolute differences from a peak at 23.6 ppm±2 ppm of 146.8, 128.4, 117.7, 95.4 and 50.5 ppm±0.1 ppm; a solid-state $^{13}$C NMR spectrum as depicted in FIG. 3 or 4 or 5; and combinations thereof.

As described above, depending on which other solid state it is compared with, crystalline Lorlatinib:Fumaric acid Form A according to the present disclosure may have advantageous properties as described above, for example improved solubility.

The present disclosure relates to crystalline Lorlatinib:Fumaric acid and a solid state form thereof. The present disclosure also relates to processes for preparation thereof, and pharmaceutical compositions including the solid state form of Lorlatinib:Fumaric acid.

In some embodiments the disclosure relates to processes for preparation of crystalline Lorlatinib:Fumaric acid.

In one embodiment the disclosure relates to a process for preparation of crystalline Lorlatinib:Fumaric acid, in embodiments crystalline Form A of Lorlatinib:Fumaric acid, wherein the process includes: a) providing Lorlatinib and Fumaric acid optionally in the form of a suspension in one or more organic solvents under heating; b) optionally stirring; c) optionally cooling; and d) optionally isolating crystalline Lorlatinib:Fumaric acid.

The process may include additional washing and drying steps.

In one embodiment Lorlatinib in step a) is provided in crystalline form, such as crystalline Lorlatinib Form 2.

In some embodiments step a) includes providing Lorlatinib and Fumaric acid in water.

In some embodiments, the process comprises:
(a) providing a mixture comprising Lorlatinib, fumaric acid and water;
(b) optionally stirring;
(c) optionally cooling; and
(d) optionally isolating the crystalline Lorlatinib:Fumaric acid Form A;
(e) optionally washing, and optionally drying.

The process may optionally comprise drying the resulting crystalline Lorlatinib:Fumaric acid form A following the isolation step.

The mixture in step (a) may be provided by adding fumaric acid to a suspension of Lorlatinib, preferably Lorlatinib Form 2, in water.

In any embodiment of the process, the suspension of Lorlatinib in water is heated, preferably to a temperature of: about 40 to about 100° C., about 60 to about 95° C., about 80 to about 95° C., preferably at about 90° C.

In any embodiment of the process, the mixture in step (a) comprises water in an amount of about 5 to 60 vol, about 10 to 50 vol, about 20 to 50 vol, about 30 to 50 vol, and preferably about 40 vol, in relation to Lorlatinib.

In any embodiment of the process, the mixture in step (a) comprises a mol ratio of Lorlatinib to fumaric acid of about 1:1.4 to about 1:0.5, or about 1:1.2 to about 1:0.6, or about 1:1 to about 1:0.6, or about 1:0.7.

In any embodiment of the process, the mixture in step (a) is heated to temperature of about 40 to about 100° C., about 60 to about 95° C., about 80 to about 95° C., preferably at about 90° C.

Preferably the mixture in step (a) is stirred. Preferably, the mixture in step (a) is stirred, preferably for about 0.5 to about 24 hours, about 0.5 to about 10 hours, about 0.5 to about 5 hours or about 0.5 to about 2 hours, or preferably about 1 hour. The stirring may be at any of the temperature ranges described above.

In any embodiment of the process, the mixture is cooled according to step (c). The cooling may be to a temperature of from: about 5° C. to about 30° C., about 10° C. to about 30° C., about 20° C. to about 30° C., or about 22° C. to about 27° C., or about 25° C. (i.e., room temperature).

In any embodiment of the process, the mixture in step (a) is heated, and step (c) comprises cooling the mixture to room temperature, and optionally maintaining at room temperature for about 0.5 to about 24 hours, about 0.5 to about 10 hours, about 0.5 to about 5 hours or about 0.5 to about 3 hours, or about 2 hours, preferably with stirring.

In any embodiment of the process, the mixture in step (a) is heated to a temperature of: about 80 to about 95° C., preferably at about 90° C. and stirred at the temperature for about 0.5 to about 2 hours, or preferably about 1 hour. Subsequently, the mixture is preferably cooled to about room temperature, preferably about 22° C. to about 27° C., or about 25° C., and stirred at this temperature for about 0.5 to about 3 hours, preferably about 2 hours.

In embodiments, there is provided a process for preparing crystalline Lorlatinib:Fumaric acid Form A according to any embodiment described herein, wherein the process comprises:
(a) providing a mixture of Lorlatinib and fumaric acid in a mole ratio of about 1:1.4 to about 1:0.5 in about 20 to 50 vol of water, in relation to Lorlatinib, at a temperature of about 60 to about 95° C.;
(b) stirring the mixture for about 0.5 to about 5 hours;
(c) cooling the mixture to about 20° C. to about 30° C., and stirring for about 0.5 to about 5 hours;
(d) isolating the crystalline Lorlatinib:Fumaric acid Form A and
(e) optionally washing, and drying.

In any embodiment of the process, crystalline Lorlatinib:Fumaric acid Form A may be isolated in step d) by any suitable means such as by filtration or by centrifuge. In an embodiment of the process, the isolation is carried out by filtration, optionally washing, preferably with water.

In any embodiment of the above described processes, the product may be dried after isolating. In embodiments, the drying is carried out in a vacuum oven. The drying may be carried out at any suitable temperature, for example, at about 30 to about 60° C., about 40 to about 50° C. or about 45° C. in a vacuum oven. Any suitable drying time may be used, for example, in embodiments the drying is carried out over a period of about 0.5 to about 24 hours, about 1 to about 15 hours, about 2 to about 5 hours, or about 3 hours. The drying may be conducted at reduced pressure or a vacuum. When the drying is carried out under reduced pressure or a vacuum, a reduced pressure of about 1 or about 200 mbar, about 1 to about 100 mbar, about 1 to 50 mbar, and particularly about 5 to about 40 mbar or more particularly, about 20 mbar, is used. Alternatively, the drying may be carried out under a flow of nitrogen or air or under vacuum. Drying under a flow of nitrogen or air may be performed at a temperature of about 20 to about 50° C., about 40 to about 50° C., and in some embodiments about 45° C.

The above processes for preparing crystalline Lorlatinib:Fumaric acid Form A according to any of the described embodiments may further include a step of combining the crystalline Lorlatinib:Fumaric acid Form A with at least one pharmaceutically acceptable excipient to form a pharmaceutical composition of pharmaceutical combination.

In another embodiment, the present disclosure encompasses use of crystalline Lorlatinib:Fumaric acid or the described solid state form thereof in the preparation of pharmaceutical compositions and/or formulations, optionally for the treatment of cancer, as detailed above.

In another embodiment, the present disclosure encompasses crystalline Lorlatinib:Fumaric acid or the described solid state form thereof for use in the preparation of pharmaceutical compositions and/or formulations, optionally for the treatment of cancer.

The present disclosure further provides pharmaceutical compositions including crystalline Lorlatinib:Fumaric acid or the described solid state form thereof according to the present disclosure.

In yet another embodiment, the present disclosure encompasses pharmaceutical formulations including crystalline Lorlatinib:Fumaric acid or the described solid state form thereof and at least one pharmaceutically acceptable excipient.

The present disclosure encompasses processes to prepare said pharmaceutical formulations of crystalline Lorlatinib:Fumaric acid by combining crystalline Lorlatinib:Fumaric acid or the described solid state form thereof and at least one pharmaceutically acceptable excipient.

Crystalline Lorlatinib:Fumaric acid or the described solid state form thereof can be used as a medicament, in embodiments for the treatment of cancer, as specified above.

The present disclosure also provides methods of treating, in embodiments for the treatment of cancer, as specified above by administering a therapeutically effective amount of crystalline Lorlatinib:Fumaric acid or of the described solid state form thereof, or at least one of the herein described pharmaceutical compositions or formulations, to a subject suffering from cancer or the above specified diseases, or otherwise in need of the treatment.

The present disclosure also provides uses of crystalline Lorlatinib:Fumaric acid of the present disclosure, or of the described solid state form thereof, or at least one of the above pharmaceutical compositions or formulations for the manufacture of medicaments, in embodiments for the treatment of cancer, as specified above.

The present disclosure encompasses processes to prepare said pharmaceutical formulations of crystalline Lorlatinib: Fumaric acid including combining the described solid state forms of crystalline Lorlatinib:Fumaric acid and at least one pharmaceutically acceptable excipient. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the administration route is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, in embodiments a powdered or granulated solid composition of the disclosure, within either a hard or soft shell. The shell can be made from gelatin and optionally contains a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of crystalline Lorlatinib:Fumaric acid can be administered. Crystalline Lorlatinib:Fumaric acid may be formulated for administration to a mammal, including a human, by oral administration. Crystalline Lorlatinib:Fumaric acid can be formulated, for example, as a tablet or capsule. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

Crystalline Lorlatinib:Fumaric acid and solid state forms defined herein as well as the pharmaceutical compositions or formulations of crystalline Lorlatinib:Fumaric acid and solid state forms thereof can be used as medicaments, in embodiments for the treatment of cancer, as specified above.

The present disclosure also provides methods of treating medicaments, in embodiments for the treatment of cancer, as specified above by administering a therapeutically effective amount of the improved solid state form of crystalline Lorlatinib:Fumaric acid of the present disclosure, or at least one of the herein described pharmaceutical compositions or formulations, to a subject suffering from the above specified diseases, or otherwise in need of the treatment.

The present disclosure also provides uses of the improved solid state form of crystalline Lorlatinib:Fumaric acid of the present disclosure, or at least one of the above pharmaceutical compositions or formulations for the manufacture of medicaments, in embodiments for the treatment of cancer, as specified above.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

XRPD Method

X-ray Powder Diffraction was performed on an X-Ray powder diffractometer Philips X'Pert PRO; CuKα radiation ($\lambda$=1.54184 Å); X'Celerator detector with active length 2.122 degrees 2-theta; using the following scanning parameters: angle range: 3-40 deg., step size 0.0167, time per step 37 s, continuous scan.

Thermal Gravimetric Analysis (TGA) Method

TGA measurements were done using TA Instruments Discovery, TG unit. About 5-10 mg of sample was weighted in open aluminum pan. Sample was purged with 50 ml/min of nitrogen flow and heated in the range of 25-300° C., with heating rate of 10° C./min.

Solid-State $^{13}$C NMR

Solid-state $^{13}$C NMR spectra were acquired on Agilent Technologies NMR System 600 MHz NMR spectrometer equipped with 3.2 mm NB dual resonance HX MAS probe. Larmor frequencies of proton, carbon and nitrogen nuclei were 599.44, 150.75 and 60.74 MHz, respectively. $^{13}$C NMR chemical shifts are reported relative to TMS (d 0.0 ppm). Samples were measured at 16,000 Hz ($^{1}$H—$^{13}$C CP-MAS).

EXAMPLES

Lorlatinib can be obtained by any procedure described in the literature, for example using the syntheses procedure reported in U.S. Pat. Nos. 8,680,111 and 9,133,215 (Examples 2 and 132). Lorlatinib form 2 used in the example below can be prepared according to Example 3 or the procedures described in U.S. Pat. No. 9,637,500.

Example 1: Preparation of Crystalline Lorlatinib:Fumaric Acid Form A

Lorlatinib (Form 2, 0.5 grams; assay 98.5%; 1.21 mmol) was suspended in water (20 ml) and the suspension heated at 90° C. Fumaric acid (99.0 mg, 0.85 mmol) was then added into suspension of Lorlatinib in water at 90° C. The obtained suspension was then stirred at 90° C. for 1 hour. The suspension was then cooled at room temperature (20-25° C.) and stirred for 2 hours. The product was filtered off, washed with water (1.5 ml) and dried in vacuum drier (20 mbar, 45° C.) for 3 hours to obtain 0.44 g of crystalline Lorlatinib: Fumaric acid Form A (HPLC assay: Lorlatinib 86.6%, fumaric acid 12.5%, KF: 0.48% water).

Example 2: Preparation of Crystalline Lorlatinib:Fumaric Acid Form A

Lorlatinib (Form 2, 14.32 grams; assay 96.0%; 33.81 mmol) was suspended in water (573 ml) and the suspension heated to 88° C. Fumaric acid (4.31 grams, 37.16 mmol) was then added into the suspension. The obtained suspension was then stirred at 90° C. for 5 hours. The suspension was then cooled at room temperature (20-25° C.) and stirred for 1.5 hours. The product was filtered off, washed with water (80 ml) and dried in a vacuum drier (20 mbar, 45° C.) for 5 hours to obtain crystalline Lorlatinib:Fumaric acid Form A (KF: 0.2% water).

Example 3. Preparation of Lorlatinib Form 2

(10R)-(7-di-tert-butyloxycarbonylamino)-12-fluoro-2,10,16-trimethyl-15-oxo-10,15,16,17-tetrahydro-2H-8,4-(metheno)pyrazolo[4,3-11]-[2,5,11]benzoxadiazacyclotetradecine-3-carbonitrile (6.84 grams, assay 87.6%, 10.11 mmol) was dissolved in ethyl acetate (49.1 mL) and 37% HCl (4.27 mL) was added. The reaction mixture was heated at 45-50° C. and stirred for 2 hours to complete Boc-deprotection reaction. Into the reaction mixture, water was added (184 mL) and the mixture was cooled to 20-25° C. The layers were separated and the aqueous layer washed with ethyl acetate (30.7 mL). Into aqueous layer, methylene chloride (61.4 mL) was added and the pH was adjusted to pH 9.3 using 10% solution of NaOH. Layers were separated and the aqueous layer extracted additionally with methylene chloride (49.1 mL). The organic layers were combined, washed with water (49.1 mL) and evaporated by vacuum distillation to dryness. Methanol (61.7 mL) was added and the obtained solution was heated to 55° C. Water was added (61.7 mL) drop-wise to the solution during 5 minutes. The obtained solution was then stirred overnight at 50-55° C. The obtained suspension was cooled at 0-5° C. over 2 hours and was further stirred for additional 2 hours at 0-5° C. with stirring. The suspension was filtered off and vacuum dried at 45° C. for 3 hours to obtain Lorlatinib Form 2 (assay 97.0%, water content by KF 2.20%).

The invention claimed is:

1. Anhydrous Crystalline Lorlatinib:Fumaric acid which is a co-crystal.
2. Crystalline Lorlatinib:Fumaric acid according to claim 1, wherein the molar ratio between Lorlatinib and fumaric acid is between 2:1.5 and 1.5:1.
3. A crystalline product according to claim 1, designated Form A, which is characterized by data selected from one or more of the following:
   (a) an XRPD pattern having peaks at 8.0, 11.6, 13.5, 17.1 and 18.2 degrees 2-theta±0.2 degrees 2-theta;
   (b) an XRPD pattern as depicted in FIG. 1;
   (c) a solid-state 13C NMR spectrum with signals at 170.4, 152.0, 141.3, 119.0 and 74.1 ppm±0.2 ppm;
   (d) a solid state 13C NMR spectrum having the following chemical shift absolute differences from a peak at 23.6 ppm±2 ppm of 146.8, 128.4, 117.7, 95.4 and 50.5 ppm±0.1 ppm;
   (e) a solid-state 13C NMR spectrum as depicted in FIG. 3 or 4 or 5; or
   (f) combinations of these data.
4. A crystalline product according to claim 1, designated Form A, characterized by an XRPD pattern having peaks at 8.0, 11.6, 13.5, 17.1 and 18.2 degrees 2-theta±0.2 degrees 2-theta, and also having one, two, three, four or five additional peaks selected from 13.1, 14.4, 15.7, 19.6 and 24.1 degrees two theta±0.2 degrees two theta.
5. A crystalline product according to claim 1, designated Form A, characterized by an XRPD pattern having peaks at 8.0, 11.6, 13.1, 13.5, 14.4, 15.7, 17.1 18.2, 19.6 and 24.1 degrees 2-theta±0.2 degrees 2-theta.
6. A crystalline product according to claim 1 containing not more than about 1% (w/w) or not more than about 0.5% (w/w) of water or organic solvent.
7. A crystalline product according to claim 1, which contains: no more than about 20% (w/w) of any other crystalline forms of Lorlatinib:Fumaric acid.
8. A crystalline product according to claim 1, which contains no more than about 20% (w/w) of amorphous Lorlatinib:Fumaric acid.
9. A medicament comprising the crystalline product according to claim 1.
10. A pharmaceutical composition comprising a crystalline product according to claim 1, and at least one pharmaceutically acceptable excipient.
11. A process for preparing a pharmaceutical composition, comprising combining a crystalline product according to claim 1 with at least one pharmaceutically acceptable excipient.
12. A process for the preparation of a crystalline product according to claim 1 comprising:
   (a) preparing a mixture comprising Lorlatinib and fumaric acid in water;
   (b) optionally stirring;
   (c) optionally cooling;
   (d) optionally isolating crystalline Lorlatinib:Fumaric acid from the mixture;
   (e) optionally washing and drying; and
   (f) obtaining a crystalline product according to claim 1.
13. A process according to claim 12, wherein step (a) comprises providing a mixture containing Lorlatinib Form 2 and fumaric acid in water, under heating.
14. A process according to claim 13, wherein the mixture in step (a) has a mol ratio of Lorlatinib to fumaric acid of: 1:1.4 to about 1:0.5.
15. A process according to claim 12, wherein the crystalline product obtained is crystalline Lorlatinib:Fumaric acid Form A and the process further comprises a step of combining the crystalline Lorlatinib:Fumaric acid Form A with at least one pharmaceutically acceptable excipient to form a pharmaceutical composition.
16. A method of treating cancer comprising administering a therapeutically effective amount of a crystalline product according to claim 1, to a subject in need of the treatment.

* * * * *